United States Patent [19]

Bronstein

[11] Patent Number: 4,842,599
[45] Date of Patent: Jun. 27, 1989

[54] PROSTHETIC CORNEA AND METHOD OF IMPLANTATION THEREFOR

[75] Inventor: Leonard Bronstein, Phoenix, Ariz.

[73] Assignee: Ann M. Bronstein, Phoenix, Ariz.

[21] Appl. No.: 120,329

[22] Filed: Nov. 12, 1987

Related U.S. Application Data

[63] Continuation-in-part of Ser. No. 923,893, Oct. 28, 1986, abandoned.

[51] Int. Cl.$^4$ ................................................ A61F 2/14
[52] U.S. Cl. ........................................ 623/5; 128/305
[58] Field of Search ........................................ 623/4-6; 128/305, 303 R; 427/2

[56] References Cited

U.S. PATENT DOCUMENTS

| | | | |
|---|---|---|---|
| 2,714,721 | 8/1955 | Stone, Jr. | 623/5 |
| 3,074,407 | 1/1963 | Moon et al. | 128/303 R |
| 3,562,820 | 2/1971 | Braun | 623/1 |
| 4,589,881 | 5/1986 | Pierschbacher et al. | 623/66 X |
| 4,612,012 | 9/1986 | White | 623/5 |
| 4,646,720 | 3/1987 | Peyman et al. | 623/5 X |
| 4,715,858 | 12/1987 | Lindstrom | 623/5 |

OTHER PUBLICATIONS

"Keratoprosthesis" Acrylic Optical Cylinder With Supporting Intralaminal Plate by Hernando Cardona, American Journal of Ophthalmology, vol. 54, No. 2, Aug. 1962, pp. 284–294.

*Primary Examiner*—Ronald L. Frinks
*Attorney, Agent, or Firm*—Don J. Flickinger; Jordan M. Meschkow

[57] ABSTRACT

The optical portion of a prosthetic cornea fabricated from a relatively inert, transparent, substantially rigid material is shaped to provide a correction factor consistent with the requirements of a selected patient. During implantation a receptacle for receiving the optical portion of the prosthetic cornea is formed by excising a portion of the living cornea. A stromal pocket is formed into the posterior one-third of the stroma of the living cornea receiver and an attachment portion of the prosthetic cornea is secured within the stromal pocket. The attachment portion extends outwardly from the optical portion, and apertures through the attachment portion serve to promote the transfer of nutrients and other fluids and gases as well as allowing normal fibrous tissue growth which aids in anchoring the prosthetic cornea in place over the long term. The apertures may optionally also be employed to facilitate the use of sutures during the implantation process.

42 Claims, 4 Drawing Sheets

PROSTHETIC CORNEA AND METHOD OF IMPLANTATION THEREFOR

CROSS REFERENCE TO RELATED APPLICATION

This application is a continuation-in-part of patent application Ser. No. 923,893 filed Oct. 28, 1986, now abandoned by Leonard Bronstein and also entitled PROSTHETIC CORNEA AND METHOD OF IMPLANTATION THEREFOR.

FIELD OF THE INVENTION

This invention relates to the field of ophthalmology, and, more particularly, to means and methods for correcting certain visual defects. In a further and more specific aspect, this invention concerns improvements in prostheses and methods for replacement of at least a portion of the cornea of the eye.

The Prior Art

In recent years, the medical community has directed considerable attention and effort to the substitution of defective organs with operationally effective replacements. The replacements have included both donor organs and prosthetic devices. Especially noteworthy is the field of cardiovascular medicine where success has been achieved with both types of replacements. Equal success, however, has not been achieved in the field of ophthalmology.

The eye is subject to numerous maladies and injuries which impact upon the cornea with attendant impaired vision or loss of sight. For example, injury or disease can adversely affect vision by causing the cornea to lose transparency or become irregular in curvature. Deteriorated vision resulting from refractive error includes astigmatism, myopia and hyperopia.

Most prior art attempts at the correction of visual defects related to an impaired cornea have generally been limited to the fitting of a prescription lens and to transplants utilizing donor tissue, either actual corneas or fabrications of collagen material. As will be readily recognized by those skilled in the art, the effectiveness of a prescription lens lies within defined limits. Neither have transplants provided a panacea.

Briefly, a corneal transplant typically comprises the excision to total penetration of the center section of the impaired cornea to a diameter that is comparable to the diameter of the donor tissue. The donor tissue is subsequently attached to the remaining annular portion of the impaired cornea by suturing. Thereafter, the eye is immobilized for an extended period of time to promote healing and to curtail painful irritation of and by the lid.

The initial limitations besetting corneal transplants are directly related to the donor tissue. The limited availability of donor tissue prohibits the frequent, routine performance of the operation. The donor tissue which is available, and considered usable, may itself include inherent imperfections. Accordingly, the patient is predestined to less than perfect vision and to the wearing of a corrective lens.

During the transplant operation, extreme care must be exercised to insure that the edges of the implant are in perfect apposition with the edges of the remaining portion of the cornea. Irregular stress occurring from misalignment or induced by faulty suturing will aberrate the cornea, resulting in a less than satisfactory result. Even if a transplant operation is faultlessly performed with a perfect implant, inherent characteristics of the patient's eye can still adversely affect the result. Such characteristics include aberration or stresses of the remaining portion of the cornea which are induced into the implant.

Inadequate fluid volume or pressure (which must be correct to impart or maintain the desired curvature of the central corneal area) is also a problem of great consternation. An inherent tendency for leakage exists along the suture line (junction) between the implant and the remaining portion of the excised cornea. Accordingly, in order to limit the likelihood for inducing excess pressure and to reduce the chances of leakage, it is common practice to replace less humor into the anterior chamber of the eye than was lost during excision of the cornea section. In addition to less than visual perfection, the practice can yield poor aesthetic or cosmetic results.

In the past, there have been investigations into the implantation of prosthetic corneas of diverse configurations and employing diverse techniques. None, however, have achieved substantial commercial success. Some of these prosthetic corneas have been fabricated from relatively inert, transparent materials such as methyl methacrylate. See, for example, the article entitled "Keratoprosthesis" by Hernando Cardona, M.D., which appeared in Volume 54, #2 (August, 1962) of the *American Journal of Ophthalmology* in which the historical work of De Quengsy, Nussbaum, Heusser, Von Hippel, Salzer, Dimmer and Verhoeff is discussed along with the more recent work of Dorzee, Franceschetti, Gyorffy, MacPherson and Anderson, Legrand, Stone, Barraquer, Cardona and others. Generally, the implementation of these efforts resulted in serious complications including the extrusion of the implant and the growth of membranes on the anterior and posterior layers of the cornea surrounding the implant. See also U.S. Pat. Nos. 2,714,721 to Stone and 4,612,012 to White.

It is apparent from the foregoing that contemporary state-of-the-art corneal transplant procedures fail to routinely produce predictably satisfactory results. Frequently, the implanted cornea is aberrant beyond the limits of correction by a prescription lens. It would be highly advantageous, therefore, to remedy the foregoing and other deficiencies inherent in the prior art.

OBJECTS OF THE INVENTION

In accordance with the foregoing, it is an object of the present invention to provide improvements in corneal transplant procedures.

Another object of the invention is the provision of a prosthetic cornea having ameliorated characteristics.

And another object of the invention is to provide a prosthetic cornea which is relatively immune to induced aberrations.

Still another object of the invention is the provision of a corneal implant which can be readily produced to accommodate a specific patient.

Yet another object of the invention is to provide a prosthetic cornea which is not subject to influences of the eye into which it is implanted.

Yet still another object of the invention is the provision of an improved method of corneal replacement.

And a further object of the invention is to provide a method of corneal replacement which will ensure predictable, satisfactory results.

Still a further object of the invention is the provision of a method which will materially reduce the post-operative convalescent period.

And still a further object of the invention is to provide means and method for replacing corneas which have become aberrant as a result of disease, injury, functional or genetic influence.

Yet still a further object of the invention is the provision of improvements according to the foregoing which can be simply and easily practiced by those skilled in the art utilizing known techniques and skills.

SUMMARY OF THE INVENTION

Briefly, to achieve these and other objects of the invention, there is provided a method of correcting a visual defect of the type resulting from an aberrant living cornea including the steps of fabricating an optically correct prosthetic cornea and implanting the prosthetic cornea into the living cornea. The step of fabricating the prosthetic cornea includes the substeps of examining the living cornea to determine a correction factor and a size and shape factor and incorporating these factors into the prosthetic cornea. The step of implanting the prosthetic cornea includes excising at least a portion of the living cornea to form a receptacle therein and securing the prosthetic cornea within the receptacle. Thereafter, a material is added on top of the prosthetic cornea to aid in regrowing normal tissue as a cover for the prosthetic cornea.

The prosthetic cornea of the instant invention includes an optical portion sized and shaped to be received within the receptacle in the living cornea and attachment means carried by the optical portion for securement to the remaining portion of the living cornea adjacent the receptacle. Preferably, the optical portion is in the form of a cylindrical section of a hollow sphere having inner and outer curved surfaces which cooperate to provide a predetermined correction factor for vision. Either of the surfaces may have a curvature which is selected to be continuous with the corresponding surface of the living cornea. Alternately, either surface may be coated with a layer of growth stimulant to promote growth of corneal tissue thereover from the remaining portion of the living cornea.

The attachment means includes an attachment portion extending generally outward from the optical portion. In accordance with a more specific and preferred embodiment of the invention, the attachment portion is in the form of an annular flange extending outwardly from the periphery of the optical portion and especially adapted to be received within an annular pocket formed into the remaining portion of the living cornea. It is preferred that the attachment portion be foraminous to accommodate the transfer of fluids, both gases and liquids, between the anterior and posterior surfaces of the remaining portion of the living cornea. The foraminous nature of the attachment portion can also accommodate sutures, if desired, during the implantation procedure and subsequently the growth of natural corneal tissue therethrough for further securement of the prosthesis.

Broadly, the method of implanting the prosthetic cornea into the living cornea comprises the steps of creating a receptacle in the living cornea, placing the prosthetic cornea into the receptacle and securing the prosthetic cornea to the living cornea. The receptacle can be created by excising a portion of the living cornea to define an optical portion receiving means and by forming a pocket into the remaining portion for receiving the attachment portion. The excising step includes making an endless incision into the living cornea from the anterior surface in a shape and size corresponding to the periphery of the optical portion. If desirable, the endless incision may extend through the cornea for excision of a generally cylindrical plug. Alternately, and preferably, the endless incision may be made to a predetermined depth at which point there is made an inwardly directed terminal incision to define a cavity within the living cornea for receiving the optical portion of the prosthetic cornea.

The attachment portion of the prosthetic cornea is secured by being placed into the defined limits of the annular pocket formed in the remaining portion of the living cornea. If desirable, the attachment portion may be additionally secured by suturing or adhesive bonding. Radial incisions, extending outwardly from the endless incision and communicating between the anterior surface of the living cornea and the pocket formed therein, may be made to accommodate insertion of the prosthetic cornea.

Both the dimensions of the prosthetic cornea and its precise position of emplacement are critical and must be determined with great care for each individual eye.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

FIG. 11 is a fragmentary horizontal section of the forward portion of an eyeball;

FIGS. 12A through 12L semi-schematically represent sequential steps in a method of implanting a prosthetic cornea in accordance with the teachings of the instant invention;

DETAILED DESCRIPTION OF THE PREFERRED EMBODIMENT

Figure 1:
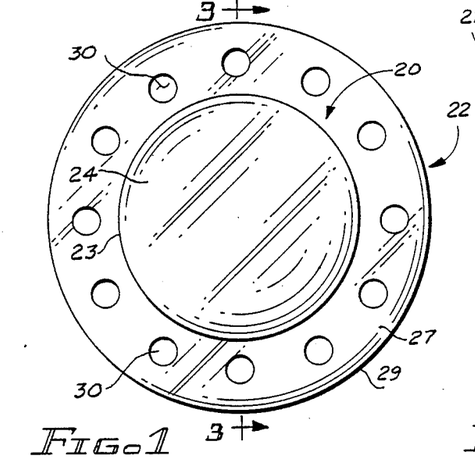
FIG. 1 is a front elevation view of a prosthetic cornea embodying the principles of the instant invention.
Figure 2:
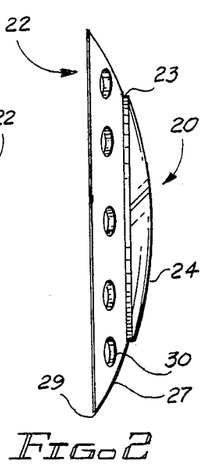
FIG. 2 is a side elevation view of the embodiment of FIG. 1.
Figure 3:
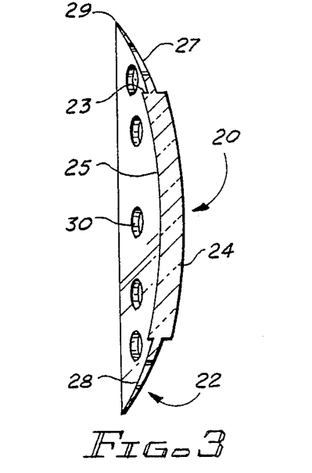
FIG. 3 is a vertical sectional view taken along the line 3—3 of FIG. 1.

Turning now to the drawings in which like reference characters indicate corresponding elements throughout the several views, attention is first directed to FIG. 1 which illustrates a prosthetic cornea, chosen for purposes of illustrating the principles of the instant invention, including an optical portion and an attachment portion generally represented by the reference characters 20 and 22, respectively. As seen in frontal elevation, the periphery of optical portion 20 is defined by circular edge 23. Optical section 20 is generally arcuate in cross-section including convex outer surface 24 and concave inner surface 25 as seen with further reference to FIGS. 2 and 3.

In accordance with the presently preferred embodiment of the invention, attachment portion 22 is in the form of an annular flange encircling optical portion 20 and extending outwardly from circular edge 23. Being substantially thinner in cross-section than optical portion 20, attachment portion 22 includes outer surface 27, inner surface 28 and concludes at the free edge with circular edge 29. A plurality of apertures 30 extend through attachment portion 22 between outer surface 27 and inner surface 28. In accordance with the embodiment herein chosen for purposes of illustration, each aperture 30 is generally circular with a preferred maximum diameter of 0.25 mm. Further, the several apertures are equiangularly spaced. As will be set forth more specifically below, the dimensions of the prosthetic cornea are critical and must be determined for each individual eye; further, as will also be discussed in more detail below, its precise emplacement position is also critical.

Figure 4:
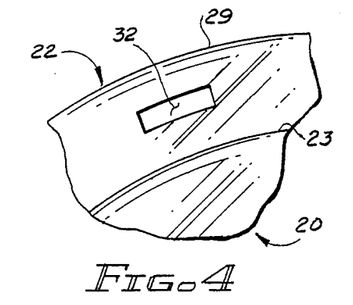
FIG. 4 is a fragmentary front elevation view generally corresponding to the illustration of FIG. 1 and showing an alternate embodiment thereof.

Referring now to FIG. 4, there is shown an alternate embodiment of the invention including optical portion 20 and attachment portion 22 as previously described. A plurality of equiangularly spaced apertures 32 extend through attachment portion 22. Each aperture 32, an alternate embodiment of previously described aperture 30, is generally elongate along an axis which is concentric with the edges 23 and 29. While the exact size of aperture 32 is readily subject to modification by those skilled in the art, it is preferred that the length of aperture 32 be approximately equal to the diameter of aperture 30 and that the width thereof be at least one-half the length.

Figure 5:
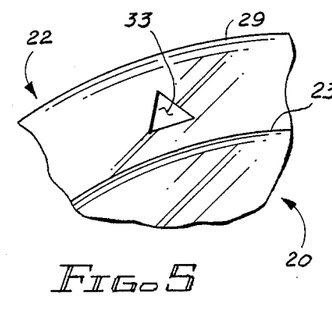
FIG. 5 is a fragmentary front elevation view generally corresponding to the illustration of FIG. 1 and showing another alternate embodiment thereof.
Figure 6:
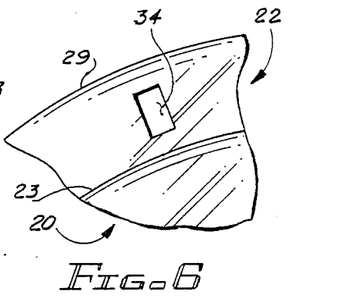
FIG. 6 is a fragmentary front elevation view generally corresponding to the illustration of FIG. 1 and showing yet another alternate embodiment thereof.
Figure 7:
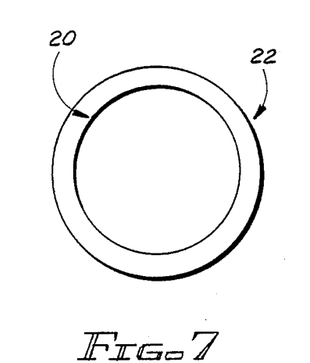
FIG. 7 is a front elevation view of still another prosthetic cornea constructed in accordance with the teachings of the instant invention.

In accordance with another alternate prosthetic cornea illustrated in FIG. 5, there is provided a plurality of equilateral apertures herein specifically illustrated as equilateral triangle 33. Preferably, equilateral triangle 33 is oriented such that one side thereof is generally tangent to a line concentric with edge 23 thereby positioning the opposite angle in opposition to edge 29. The alternate aperture 34 as seen in FIG. 6, like the previously described aperture 32, is elongate. In contrast thereto, however, aperture 34 is elongate along a radial axis. Seen in FIG. 7 is yet another embodiment in which attachment portion 22 is continuous throughout and devoid of apertures.

Figure 8:
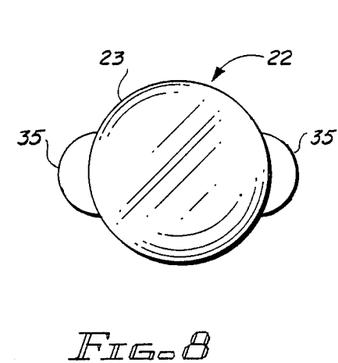
FIG. 8 is a front elevation of another prosthetic cornea of the instant invention.

Other variantly configured attachment portions are contemplated by the instant invention. For example, there is seen in FIG. 8 an attachment portion in the form of a pair of tabs or ears 35 which extend in diametrically opposed directions from optical portion 20. A second pair of diametrically opposed tabs 37, spaced intermediate the tabs 35, are included in the embodiment of FIG. 9.

Further description of the prosthetic cornea of the instant invention, including alternate embodiments, the manner and process of their fabrication and their function, will be made presently.

Figure 10:
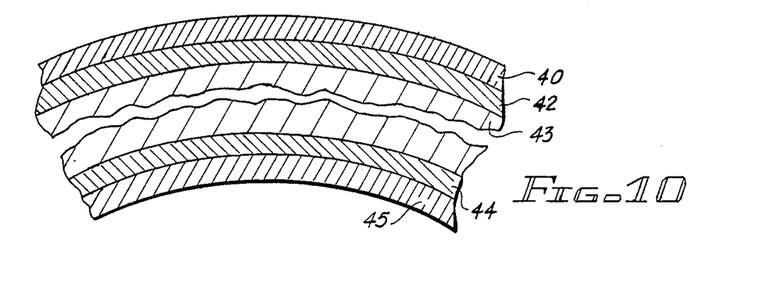
FIG. 10 is a fragmentary cross-section of the cornea of a human eye, set forth herein for purposes of orientation and understanding.

For purposes of reference and understanding during the detailed description of the subject prosthetic cornea and the method of its implantation which follows, there is set forth in FIG. 10 a fragmentary section of a natural cornea. Intended to be typical of the normal cornea, the section illustrates the several layers which form the cornea tissue structure. The several layers are, in order from the anterior side, the epithelium 40, Bowman's membrane 42, stroma 43, Descemet's membrane 44 and endothelium 45. In the healthy eye, the tissue of the cornea (in accordance with the generally accepted norm) has a central thickness of approximately 0.5 mm, and the periphery is normally somewhat thicker. The stroma, being the thickest layer, represents on the order of 90% of the total thickness of the cornea, and the other four layers together represent approximately 10% of the corneal thickness. As will be appreciated by those skilled in the art, the dimensions are subject to individual variation and require measurement by a trained practitioner.

It is of particular importance to appreciate that the stroma does not have uniform viscous characteristics across its thickness. Rather, the front or anterior region is substantially more fluid than the back or posterior region of the stroma. The reason for the importance of this characteristic will become more apparent as the description of the invention proceeds.

Figures 11, 12A, 12B, 12C, 12F, 12G, 12H, 12I:
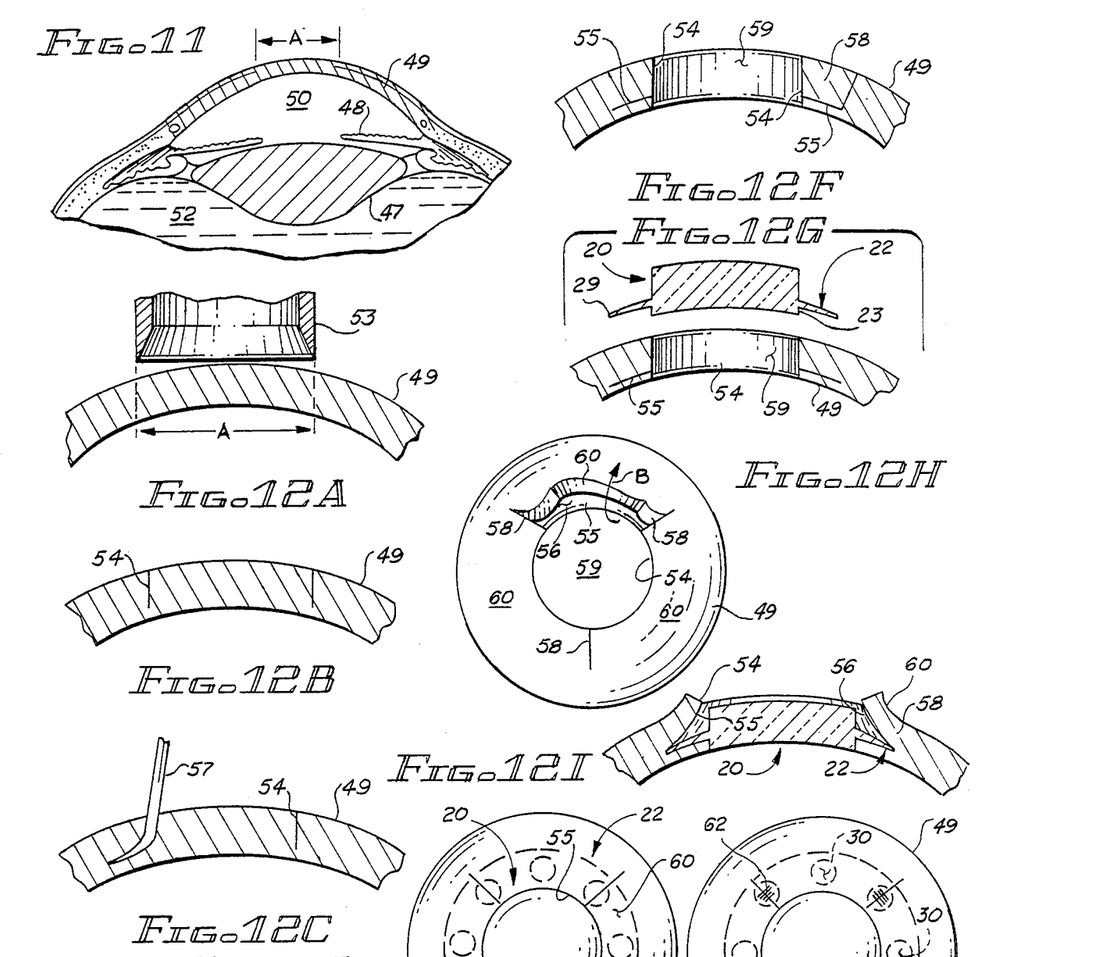

Implantation of the prosthetic cornea, in accordance with one embodiment of the instant invention, is initiated by defining the area of the aberrant cornea to be removed. With reference to FIG. 11, there is seen in section the forward portion of a typical eyeball including the crystalline lens 47, the iris 48 and the cornea 49. The anterior chamber 50 resides intermediate the crystalline lens 47 and the cornea 49. A cavity 52 occupied by vitreous humor is located behind the crystalline lens. Other details and features of the eyeball, and of the tissue section seen in FIG. 10 not herein illustrated and described, will be readily apparent to those skilled in the art.

The section of the aberrant cornea to be removed is generally circular in cross section, the diameter of which is defined by the dimension A. The diameter of the circular section, which corresponds to the outside diameter of the optical portion of the prosthetic cornea to be implanted, should be as large as possible (considering other dimensional constraints to be discussed below) to eliminate or minimize optical flare effects. It has been found that a diameter of about 5.0 mm, which is approximately the chord diameter of the finest focusing area of the cornea, is an acceptable (average) size for many eyes and that a diameter of less than about 3.0 mm results in the aforementioned optical flare effects. Thus, a diameter of 3.0 mm for the optical portion of the prosthetic cornea (and hence for the dimension A) may be considered a practical lower limit.

The overall diameter of the corneal implant must be smaller than the visible iris diameter by at least 3.0 millimeters; i.e., there should be a minimum distance of approximately 1.5 mm. from the edge of the cornea on all sides. It has been found that, if a space or swelling is created in the stroma too close to the edge of the cornea, the normally avascular cornea will allow blood vessels to invade the tissue because the blood vessels will creep into the cornea wherever a space is created large enough for a blood vessel to invade.

Because it is desirable to have the optical portion as large as possible (and the attachment portion as stable as possible), the optical portion should be approximately 2.0 to 3.0 mm smaller than the diameter of the attachment portion. As an example, if the visible iris diameter is 12.0 mm, the largest overall diameter of the implant could be as large as 9.0 mm, and the optical portion could be as large as 7.0 mm. However, for a 10.0 mm visible iris diameter, the largest overall diameter could be 7.0 mm and the largest optical portion could be 5.0 mm. In one presently preferred embodiment, the overall diameter (i.e., the diameter of the attachment portion) is established as 3.5 mm to 4.0 mm smaller than the visible iris diameter, and the optical portion is established as approximately 2.5 mm to 3.0 mm smaller than the overall diameter, but as large as possible.

Again, it must be understood that if the overall diameter of the prosthetic cornea is too large, spaces will be created which will allow blood vessels to invade the cornea. If the optical portion is too small, optical flare can be created which interferes with vision.

Turning now to FIG. 12A, it is seen that the designated cylindrical section of cornea 49 is removed with a trephine 53 of appropriate diameter. The use of a trephine to excise a selected portion of the cornea of an eye involves techniques and procedures familiar to those skilled in the art in that, during the initial steps of a present day cornea transplant operation, the central section of the cornea is completely excised to a diameter comparable to that of the donor tissue.

In accordance with the teachings of the presently discussed instant invention, as specifically illustrated in FIG. 12B, the initial cut with the trephine is to an intermediate depth of the cornea, and, more particularly, into the posterior $\frac{1}{3}$ of the stroma. The minimum depth of this cut (i.e., through at least anterior $\frac{2}{3}$ of the stroma) is of crucial importance as will be discussed further below. The incision, which is represented by the line 54, is best described as a cylindrical sidewall.

Figure 12D:
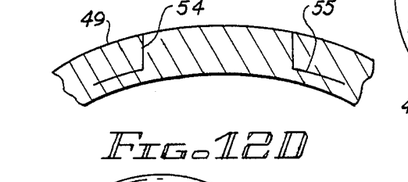

Subsequently, as illustrated in FIGS. 12C and 12D, there is made an annular incision 55 extending radially outwardly from the lower end of the initial cylindrical incision 54. The incision can be readily made and additional tissue removed to provide what is best described as a stromal pocket 56, as best seen with reference to FIGS. 12H to 12I, to accommodate the thickness of the attachment portion of the prosthetic cornea by the use of a Lamellar dissector 57, or similar instrument, entered through the incision 54.

Figure 12E:
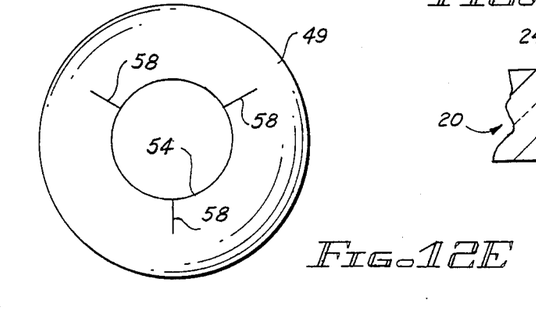

Preparation of the aberrant cornea is continued, as viewed in FIGS. 12E and 12F, by removing additional tissue as may be necessary to conform the stromal pocket to the dimensions of the attachment portion of the prosthetic cornea to be used. If necessary, one or more radial incisions 58 may also be made to subsequently facilitate introduction of the attachment portion into the stromal pocket; however, it is presently preferred that no radial incisions 58 be used unless the dimensions of the prosthetic implant and the elasticity of the tissue of the eye being implanted obviate their necessity. If the radial incisions 58 are deemed necessary for a given implant, each is made through the epithelium to a depth which terminates at the stromal pocket 56. Further, each incision 58 may extend radially outwardly from the cylindrical incision 54 to a point which corresponds to the periphery of the stromal pocket 56.

When Descemets Membrane and Endothelium are opaque, which is rare, completion of the preparation also includes continuing cylindrical incision 54 through the remaining posterior corneal layers, thereby excising the predetermined corneal section. Opening 59, having a sidewall defined by incision 54, now extends through the cornea 49. In view of the thickness of the cornea and the fact that incision 54 is endless, opening 59 is considered to be cylindrical. If complete penetration is to be produced, prior to creating complete penetration, sutures are affixed to the anterior cornea above the stromal pocket, so that the stromal pocket may be held open when the cornea collapses due to fluid loss. These sutures are removed after the prosthetic is in place and replacement fluid is placed into the anterior chamber and the prosthetic is shown to be positioned properly.

The several previously described incisions form a receptacle within cornea 49 which is sized and shaped to receive a selected one of the previously described prosthetic corneas of the instant invention. As more specifically illustrated in FIG. 12G, it is preferred that opening 59 be sized to closely receive the edge 23 of optical portion 20. The stromal pocket 56 is of sufficient radial width and fore and aft thickness to just receive attachment portion 22 of the prosthetic cornea.

As mentioned above, the attachment portion 22 of the prosthetic cornea must reside in the posterior $\frac{1}{3}$ of the stroma; thus, it must, by definition, be no thicker than $\frac{1}{3}$ of the thickness of the stroma. The reason for restricting the attachment portion 22 of the prosthetic cornea to the posterior $\frac{1}{3}$ of the cornea is the recognition that most of the flow of nutrient to the cornea from the limbus is through the more fluid anterior portion of the stroma. It has been found that, if the attachment portion of the prosthetic cornea is not emplaced in the posterior $\frac{1}{3}$ of the stroma, edema, vascularization and eventual extrusion results, a chronic problem of the prior art implantations.

The size of the apertures 30, 32, 33, 34 through the flange constituting the attachment portion 22 of the prosthetic cornea should be sufficiently large not only to receive sutures (if used) during the emplacement process and to admit growth of tissue to permanently fix the implant in place, but also to transfer fluids and nutrients, both liquids and gases across the attachment portion. However, if the apertures are too large, a fluid pocket occurs which can create corneal breakdown or delay healing time. The maximum diameter should be no larger than 0.25 mm, and preferably in the range of 0.10 mm to 0.15 mm.

Another factor determining the dimensions and precise configuration of the prosthetic cornea is the curvature of the annular attachment portion 22. In certain specific implantations, it is even beneficial to have slightly different curvatures to the anterior and posterior surfaces of the attachment portion. In order to prevent the establishment of permanent mechanical stresses which would tend to distort the eyeball, the anterior surface of the attachment portion 22 should have the same curvature as the anterior surface of the normal cornea, and the posterior surface of the attachment portion should have the same or a slightly flatter curvature than the posterior curve of the cornea to positively avoid establishing a trapped fluid or gaseous pocket which affects optics and delays healing.

The implantation phase of the method of the first embodiment of the instant invention commences with placement of the prosthetic cornea within the receptacle formed during the previously described preparation phase. In the preferred method in which no radial incisions 58 are used, the prosthetic cornea is introduced at an angle into the receptacle to start a section of the attachment portion periphery into the stromal pocket. Then, utilizing the Lamillar dissector or other similar instrument in the fashion of a "tire iron", the remainder of the attachment portion is slipped into the stromal pocket. If radial incisions 58 are employed, they (in cooperation with the stromal pocket 56) define a one or more flaps 60, each lying between adjacent incisions 58. The flaps 60 can be lifted upwardly and outwardly in a direction defined by the arcuate arrowed line B in FIG. 12H to facilitate insertion of the prosthetic cornea into the receptacle as best illustrated in connection with FIG. 12I. After insertion of the prosthetic cornea into the receptacle, the flaps 60 are returned to the normal or original position as seen in FIG. 12J. Again, it is presently preferred to use as few flaps 60 as possible with a given implant, and it is especially preferred to use none at all if possible, use of only a single flap being next most preferred.

With further reference to FIG. 12J, it is seen that after emplacement of the prosthetic cornea, annular flange-like attachment portion 22 is captively retained within the stromal pocket 56 in the posterior ⅓ of the stroma. The sidewall created by incision 54 abuts the peripheral edge 23 of optical portion 20. The several incisions 58, if desired, may be closed by sutures 62 as illustrated in FIG. 12K. The sutures 62 may extend through the apertures 30 to prevent movement or shifting of the prosthetic cornea during the subsequent convalescent period.

Figure 12L:
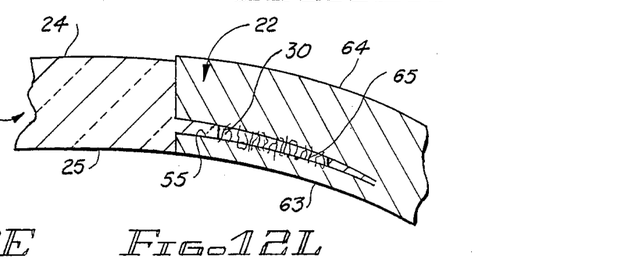

It is within the scope of the instant invention, that the prosthetic cornea be selected such that the thickness of the optical portion be less than the thickness of the live cornea into which it is implanted. As seen in FIG. 12L, the stromal pocket is formed at a location such that the posterior surface 63 of the live cornea and the posterior surface 25 of the optical portion are substantially continuous. The difference in thickness, therefore, appears between the anterior surface 64 of the live cornea and the outer surface 24 of optical section 20. Preferably, the thickness of the optical portion should be such that the anterior surface is at the anterior surface of the stroma. Accordingly, epithelial growth can proceed over the surface 24 of the prosthetic cornea thereby resulting in a smooth transition at the juncture of the cornea and the prosthesis. The transition is important to prevent irritation to and from the eye lid of the patient. The growth also prevents epithelial breakdown of the edges of the remaining cornea.

Prior to, during or (preferably) subsequent to the implantation procedure, surface 24 may be coated with an epithelium growth stimulant, such as silicon dioxide, fibronectin (especially preferred), polypeptide, or other available product. The initial thickness of the coating may be selected to provide a substantially continuous anterior surface of the cornea.

It is presently preferred that sutures not be used during the implantation process; but, if they are used, sutures 62 can be of the commercially available self-dissolving type. The fibrous tissues of the cornea tend to grow rather rapidly; therefore, as the sutures dissolve, fibrous growth 65, as seen in FIG. 12L, will occur within and through the apertures 30. Upon total dissolution of the sutures, the permanence of the implant in its correct position will be assisted by the natural growth extending through the several apertures. As previously mentioned, the apertures 30 further permanently accommodate the passage of fluids and gaseous exchange between the anterior and posterior surfaces of the cornea in the region of the attachment portion of the prosthetic cornea.

The method of implanting a prosthetic cornea, as described in detail in connection with FIGS. 12A through 12L, is well adapted for correcting errors of the type where the natural cornea displays less than satisfactory transparency throughout the total thickness of the cornea. While this is very rare, in cases where the cornea is either translucent or opaque throughout its total thickness, it is generally considered necessary to remove the full depth of corneal tissue and to replace the removed tissue with a prosthesis. However, and as a preferred embodiment, also contemplated by the instant invention is a method of prosthetic corneal implantation especially adapted for correcting aberrations of the type attributable to surface irregularities or lack of transparency no deeper than the stroma. Even though the cornea may be clear, vision is distorted. Exemplary are keratoconus, astigmatism, myopia and hyperopia.

In addition, it has been found that the procedure employing total penetration excision of tissue followed by the implantation of a prosthetic cornea is often unsatisfactory for subtle reasons. If the posterior surface of the prosthetic cornea is even slightly rearward of the back surface of the surrounding corneal tissue, there is a tendency to collect debris at the back surface of the prosthetic cornea with a consequent gradual loss of optical properties. Even if the posterior surface of the prosthetic cornea is perfectly aligned with the surrounding tissue, aqueous fluid tends to seep into the junction between the prosthetic cornea and the surrounding tissue causing edema and the consequent unsatisfactory results. An effective seal to the rear of the prosthetic cornea must be realized to prevent these problems, and this may be achieved, even for the problems usually addressed with a full penetration procedure, by a procedure which falls just short of full penetration as will now be discussed.

With reference to FIGS. 13A through 13D, it is seen that the instant method commences with steps which are analogous to the initial steps of the previously described method. Trephine 53 is initially utilized to make endless incision 54 encompassing the aberrant area of the living cornea to be replaced by a prosthesis. Incision 54 is made to a predetermined depth (preferably to or very near the junction of the stroma and Descemet's membrane) after which Lamellar dissector 57 is utilized to form annular incision 55 defining the stromal pocket. Thereafter, modifications and variations of the procedure are apparent.

Once the cylindrical incision 54 terminates at the juncture of the stroma and Descemet's membrane, generally circular and inwardly directed terminal incision 70 is then made at the nethermost portion of endless incision 54 to facilitate removal of cylindrical plug 72. Terminal incision 70 is readily made as by the use of Lamellar dissector 57 being entered through incision 54 and having the tip directed inwardly. Ideally, terminal incision 70 lies along the contact area between the stroma and Descemet's membrane, and this step can be repeated at different depths (working inwardly from a position slightly outwardly from the junction) to insure that there is no penetration through Descemet's membrane. As a result of contrasting visual characteristics, the stroma and Descemet's membrane are readily discernible.

Figure 13A:
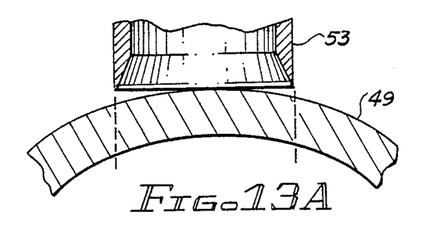
FIGS. 13A through 13K semi-schematically depict sequential steps in an alternate method of implanting a prosthetic cornea in accordance with the teachings of the instant invention.
Figure 13B:
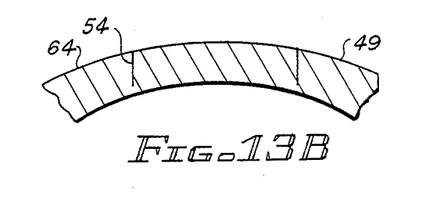
Figure 13C:
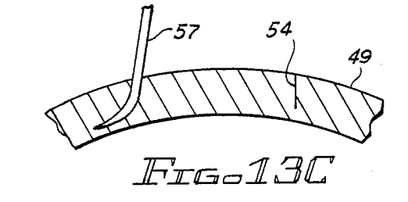
Figure 13D:
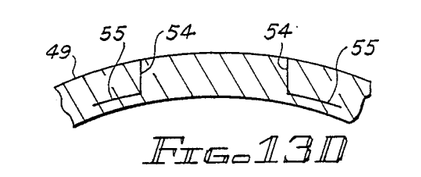
Figure 13E:
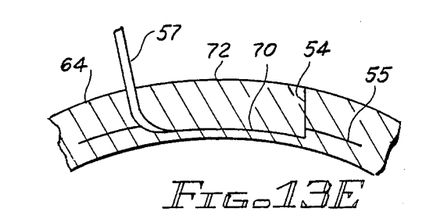
Figures 13F, 13K:
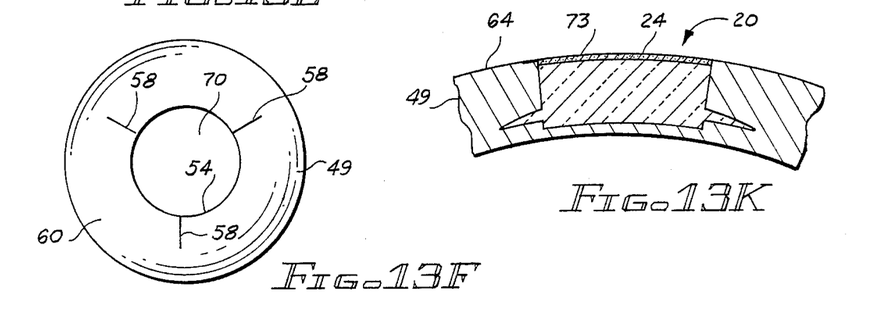
Figure 13G:
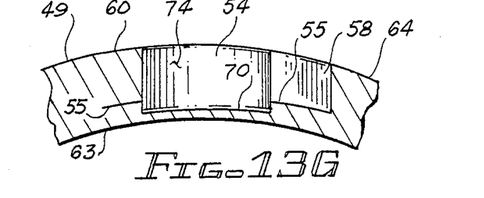

As a variation, incision 54 may initially extend to the total desired depth. This is considered optional with the surgeon performing the procedure. Among other options is the making of radial incisions 58 to create frontal flaps 60 as seen in FIGS. 13F and 13G and as described in detail in connection with the previous method of implantation.

The removal of cylindrical plug 72 creates cylindrical cavity 74 which is abounded by a sidewall and bottom 70. The several incisions, cylindrical incision 54, annular incision 55, terminal incision 70 and optional radial incisions 58, define a receptacle for receiving the selected prosthetic cornea which includes stromal pocket 56 prepared as previously described. It is especially noted that after formation of the receptacle, the posterior portion of the living cornea remains intact. The layers immediately adjacent posterior surface 63, Descemet's membrane 44 and endothelium 45, have not been excised and are integral with the remaining portion of the living cornea. Accordingly, there is no loss of fluid from within the eye.

The previously described receptacle is sized and shaped to receive a prosthetic cornea of the type as previously herein described in detail. As will be appreciated by those skilled in the art, the thickness of the optical portion 20 is determined by the depth of cylindrical cavity 74. Similarly, attachment portion 22 resides at a location relative outer surface 24 and inner surface 25 which corresponds to the location of stromal pocket 56 relative anterior surface 64 and posterior surface 65 of the living cornea. Optionally, outer surface 24 may be coated with a growth stimulant material prior to implantation of the prosthetic cornea into the receptacle formed within the living cornea.

Figure 13H:
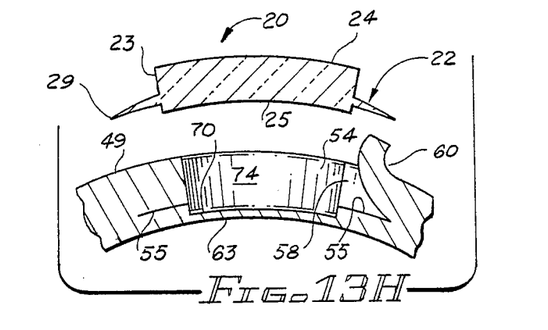
Figure 13I:
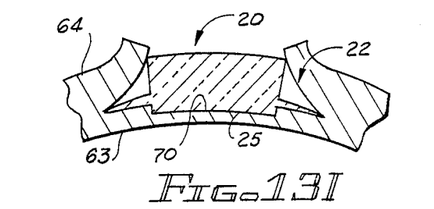

As illustrated in FIGS. 13H and 13I placement of the prosthetic cornea into the living cornea is generally analogous to the corresponding steps of the previously described method. In contrast thereto, however, inner surface 25 of the prosthetic cornea is placed in juxtaposition with terminal incision 70. Thereafter, the attachment portion 22 is naturally secured within stromal pocket 56. In some instances, the securement may be augmented by adhesive bonding, suturing or other expediency.

Figure 13J:
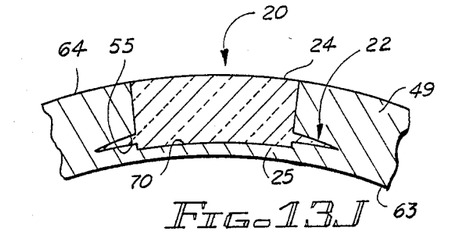

As previously noted, anterior surface 24 of optical portion 20 of the prosthetic cornea is preferably coated with a growth stimulant. However, if a growth stimulant is not laid over anterior surface 24, the thickness of the optical portion 20 is chosen to correspond with the depth of cylindrical cavity 74 such that after implantation, as specifically seen in FIG. 13J, anterior surface 24 of the prosthetic cornea is substantially continuous with the anterior surface 64 of the living cornea. Alternately and preferably, as illustrated in FIG. 13K, the thickness of optical portion 20 may be less than the depth of opening 74 such that surface 24 is recessed below the surface 64 thereby providing for a coating of growth stimulant 73. Preferably, the dimension between the surfaces 24 and 64 generally corresponds to the thickness of the anterior-most layer, the epithelium, of the living cornea and Bowman's membrane. Ideally, growth stimulant 73 may be applied to surface 24 in a thickness also substantially equal to the thickness of the epithelium thereby initially providing a continuous outer surface of the cornea which will not irritate the eye and which will protect the relatively delicate tissue at the juncture of incision 54 and anterior surface 64. As a practical matter, it has been found that the thickness of the layer of growth stimulant is not critical. Through the selection of a biodegradable material, the growth stimulant may recede in direct proportion to the growth of the epithelium over surface 24.

Figure 14A:
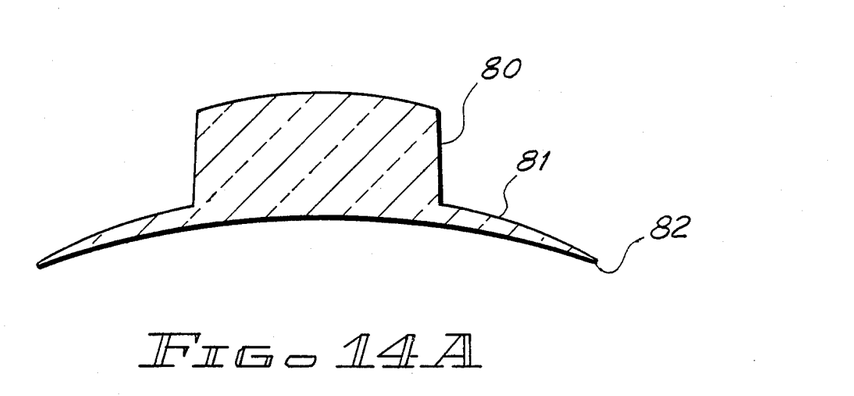
FIGS. 14A and 14B illustrate a variant configuration for the subject prosthetic cornea, respectively, before and after implantation.
Figure 14B:
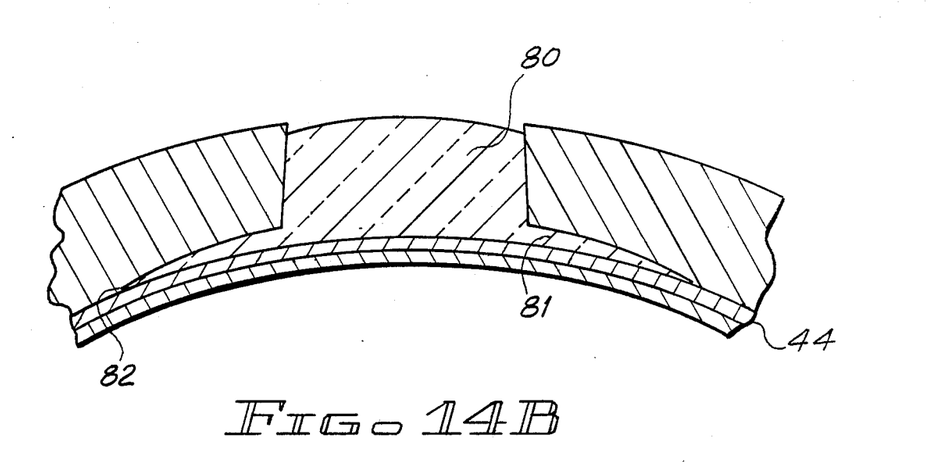

Referring now to FIGS. 14a and 14b, there is shown a variant configuration for the prosthetic cornea. In this configuration, the posterior surfaces of the optical portion 80 and the attachment portion 81 are coextensive. As a result, the entire area of the continuous surface may rest on the anterior surface of Descemet's membrane 44 or be flatter so that only the central optic approaches the curvature of the membrane 44.

Another highly desirable feature (which may be incorporated into any of the prosthetic cornea configurations discussed above) of the embodiment illustrated in FIGS. 14a and 14b is the manner in which the attachment portion 81 tapers to a fine edge 82 at its periphery. It has been found that incorporation of this feature further constrains against undesirable subsequent vascularization in the region because it eliminates the formation of an unwanted space in the living cornea in the peripheral region of the stromal pocket, a condition which is otherwise promoted by a relatively blunt edge of significant thickness to the attachment portion.

The prosthetic cornea of the instant invention is readily fabricated utilizing techniques and procedures familiar to those skilled in the manufacture of contact lens. Preferably, the materials are chosen from the group of inherently rigid plastics which includes polymethyl methacrylate, polycarbonate and silicone acrylates. Such materials, which have a proven compatibility with the tissues of the eye, can be readily molded or machine cut into shapes of inherent stability. Further, the inner and outer surfaces of the optical material may be shaped and optically polished as necessary to provide proper visual characteristics for an individual patient.

Being relatively rigid, such materials are substantially immune to stresses induced during either the implantation procedure or by the remaining live cornea. Parameters for fabrication of the desired lens can be readily determined by those skilled in the art utilizing the "Corneascope", "Kerascan" computer and other familiar instruments (although it should be noted that the area of measurement of a conventional keratometer is insufficient for making the necessary measurements). The "Corneascope", for example, will provide measurements of the curvature of the cornea at the center and at the periphery. Measurements of the refractive error can be made by retinoscopy. Pachymetry will provide corneal thickness measurements. The area of the cornea to be repaired, and accordingly the size, thickness and curvature of the prosthetic cornea to be fabricated and implanted, can be readily determined from the foregoing data.

As previously noted, the surfaces of the prosthetic cornea may be shaped as necessary to provide proper visual characteristics for an individual patient. More specifically and with particular reference to the optical portion, the correction of myopia requires that the outer surface be somewhat flatter than the inner surface. The opposite, a somewhat steeper curvature to the outer surface, is required for the correction of hyperopia. For patients normally requiring bifocal prescription lens, the prosthetic cornea can be made to be aspheric. The instant invention also contemplates a remedy for those having undergone cataract removal and are aphakic. To remedy this malady, the prosthetic cornea may be fabricated with a flatter than normal inner surface and a steeper than normal outer surface. While the radius of curvature is variable to provide the desired corrective factor, the inner and the outer surfaces of the optical portion of the prosthetic cornea are spherical, thereby negating considerations of astigmatism. It is also within the scope of the instant invention that certain defects and aberrations existing in the remaining corneal tissue may be remedied by implantation of the previously described prosthetic cornea. In the preferred embodiment, the attachment portion is an annular section of a hollow sphere. Placement of the attachment portion within the stromal pocket has a direct effect upon the remaining corneal tissue. The radius of curvature of the sphere can be increased or decreased as necessary to raise or lower, respectively, the remaining corneal tissue. Accordingly, substantially the entire cornea, the remaining living tissue and the prosthesis, can be brought into a desired curvature.

The means of fabrication of a prosthetic cornea of the instant invention from selected plastics as set forth above are applicable to the fabrication of prosthesis utilizing other materials such as donor tissue corneas and collagen corneas. After being frozen, the donor tissue or the collagen tissue can be formed into a shape suitable to be implanted within a receptacle created by incisions as previously described. Best described as soft tissue prosthesis, the implants will still be subject to certain aberration producing stresses. However, the precision of mounting will be substantially improved and suture induced aberrations will be minimized.

Figure 9:
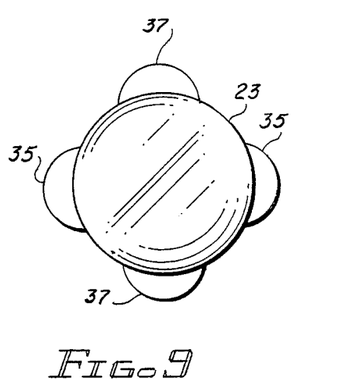
FIG. 9 is a front elevation of still another embodiment of a prosthetic cornea of the instant invention.

Chosen for purposes of illustration herein, was a method of implantation involving the optional use of sutures. The embodiments of the prosthetic cornea of the instant invention specifically illustrated in FIGS. 1-6 are provided with apertures which may accommodate suturing. It is noted that the attachment portions seen in the embodiments of FIGS. 7-9 are without apertures. The latter embodiments are especially adapted to be implanted and affixed to the remaining corneal tissue by selected bonding agents such as collagen glue, cyanoacrylate adhesives, or mussel glue (or even employing no special affixing agent at all). Such bonding agents, if used, may become biodegradable with time. However, normal tissue growth and development will serve to positionally maintain and effectively seal the prosthetic cornea within a relatively short period of time.

As will be appreciated by those skilled in the art, bonding agents may be used as an adjunct to the use of sutures. Also, to promote fluid flow, apertures may be incorporated into the attachment portion of a prosthetic cornea which is implanted exclusively with the use of bonding agents.

The method of implantation illustrated in FIGS. 12 and 13 suggests the creation of three equiangularly spaced radial incisions 58. It was to be understood that such was chosen for purpose of illustration. Any desired number of radial incisions (or none at all) may be formed. Such radial incisions are preferred as mandated by the size of the attachment means and the character of the remaining live corneal tissue and individual preference of the surgeon. Alternately, the radial incisions may be eliminated and the attachment portion of the prosthetic cornea inserted into the stromal pocket utilizing the elasticity of the live corneal tissue.

Various changes and modifications to the embodiments herein chosen for purposes of illustrations will readily occur to those skilled in the art. To the extent that such modifications and variations do not depart from the spirit of the invention, they are intended to be included within the scope thereof which is assessed only by a fair interpretation of the following claims.

Having fully described and disclosed the instant invention and alternately preferred embodiments thereof in such clear and concise terms as to enable those skilled in the art to understand and practice the same, the invention claimed is:

1. A unitary prosthetic cornea for implantation into a living cornea, which living cornea includes:
   (A) a receptacle formed therein as a result of the excision of an aberrated section of predetermined dimension and to a predetermined depth terminating in the posterior one-third of the stroma;
   (B) a remaining portion adjacent the receptacle;
   (C) a posterior surface; and
   (D) an annular stromal pocket formed continuous with and extending outwardly from said receptacle, said stromal pocket residing within the posterior one-third of the stroma;

and for correcting defects inherent in said aberrated section, said prosthetic cornea:
   (E) being formed of a material which is relatively inert, transparent and substantially rigid;

said prosthetic cornea further comprising:
   (F) an optical portion sized and shaped to be received within the receptacle in said living cornea; and
   (G) an attachment portion carried by said optical portion for securement to the remaining portion of said living cornea, said attachment portion including an annular flange extending generally outwardly from said optical portion, said annular flange:
      (1) being dimensioned and configured and positioned with respect to said optical portion to be received within said stromal pocket and to reside entirely within the posterior one-third of the stroma; and
      (2) including a plurality of circumferentially distributed apertures therethrough, said apertures being of sufficient diameter to transfer fluids through said annular flange.

2. The prosthetic cornea of claim 1 in which:
   (A) said optical portion is generally cylindrical; and
   (B) said annular flange is characterized by having a circular outer periphery, said annular flange tapering in thickness to a fine edge at said outer periphery.

3. The prosthetic cornea of claim 2 in which said optical portion includes:
   (A) an outer surface;
   (B) an inner surface; and
   (C) a thickness of predetermined dimension between said outer and inner surfaces which is less than the predetermined depth of the receptacle by an amount approximately equal to the combined thickness of the epithelium and Bowman's membrane.

4. The prosthetic cornea of claim 3 which further includes a layer of growth stimulant carried on at least one of said outer and inner surfaces of said optical portion.

5. The prosthetic cornea of claim 4 in which said growth stimulant is characterized as being biodegradable.

6. The prosthetic cornea of claim 4 in which said growth stimulant is chosen from the group including:
   (A) silicon dioxide;
   (B) fibronectin; and
   (C) polypeptide.

7. The prosthetic cornea of claim 6 in which said apertures through said annular flange are of sufficiently large size to receive sutures therethrough for securing said attachment portion to the remaining portion of said living cornea.

8. The prosthetic cornea of claim 7 in which said apertures are generally cylindrical.

9. The prosthetic cornea of claim 7 in which said apertures are generally elongate.

10. The prosthetic cornea of claim 7 in which said apertures are generally equilateral.

11. The prosthetic cornea of claim 7 in which the material of fabrication is chosen from the group including polymethyl methacrylate, polycarbonate and silicone acrylate.

12. The prosthetic cornea of claim 4 in which:
   (A) said outer surface of said optical portion is generally curved;
   (B) said inner surface of said optical portion is generally curved; and
   (C) said arcuate outer surface cooperates with said inner surface to provide a correction factor for vision.

13. The prosthetic cornea of claim 12 in which said curved inner surface has a curvature which is selected to be continuous with the posterior surface of said living cornea defining the lower terminus of said receptacle.

14. The prosthetic cornea of claim 13 in which said curved outer surface has a curvature which is selected to be continuous with the anterior surface of said living cornea.

15. The prosthetic cornea of claim 2 further dimensionally characterized in that:
   (A) all portions of said prosthetic cornea are situated at least 1.5 mm from any part of the limbus; and
   (B) the minimum diameter of said optical portion is 3.0 mm.

16. The prosthetic cornea of claim 3 further dimensionally characterized in that:
   (A) all portions of said prosthetic cornea are situated at least 1.5 mm from any part of the limbus; and
   (B) the minimum diameter of said optical portion is 3.0 mm.

17. The prosthetic cornea of claim 6 further dimensionally characterized in that:
   (A) all portions of said prosthetic cornea are situated at least 1.5 mm from any part of the limbus; and
   (B) the minimum diameter of said optical portion is 3.0 mm.

18. The prosthetic cornea of claim 7 further dimensionally characterized in that:
   (A) all portions of said prosthetic cornea are situated at least 1.5 mm from any part of the limbus; and
   (B) the minimum diameter of said optical portion is 3.0 mm.

19. The prosthetic cornea of claim 12 further dimensonally characterized in that:
   (A) all portions of said prosthetic cornea are situated at least 1.5 mm from any part of the limbus; and
   (B) the minimum diameter of said optical portion is 3.0 mm.

20. The prosthetic cornea of claim 13 further dimensionally characterized in that:
   (A) all portions of said prosthetic cornea are situated at least 1.5 mm from any part of the limbus; and
   (B) the minimum diameter of said optical portion is 3.0 mm.

21. The prosthetic cornea of claim 14 further dimensionally characterized in that:
   (A) all portions of said prosthetic cornea are situated at least 1.5 mm from any part of the limbus; and
   (B) the minimum diameter of said optical portion is 3.0 mm.

22. The prosthetic cornea of claim 15 in which a lower surface of said annular flange is formed continuously with said inner surface of said optical portion.

23. The prosthetic cornea of claim 16 in which a lower surface of said annular flange is formed continuously with said inner surface of said optical portion.

24. The prosthetic cornea of claim 17 in which a lower surface of said annular flange is formed continuously with said inner surface of said optical portion.

25. The prosthetic cornea of claim 18 in which a lower surface of said annular flange is formed continuously with said inner surface of said optical portion.

26. The prosthetic cornea of claim 19 in which a lower surface of said annular flange is formed continuously with said inner surface of said optical portion.

27. The prosthetic cornea of claim 20 in which a lower surface of said annular flange is formed continuously with said inner surface of said optical portion.

28. The prosthetic cornea of claim 21 in which a lower surface of said annular flange is formed continuously with said inner surface of said optical portion.

29. A method of implanting a prosthetic cornea into the living cornea of an eyeball, which prosthetic cornea is formed of a material which is relatively inert, transparent and substantially rigid and which includes:
   (A) cylindrical optical portion having spaced apart inner and outer surfaces and a periphery; and
   (B) an attachment portion extending outwardly from the periphery of the optical portion and including an annular flange extending generally radially outwardly from said optical portion, the annular flange including a plurality of circumferentially distributed apertures therethrough, the apertures being of sufficient diameter to transfer fluids through the annular flange;
and which living cornea includes:
   (C) spaced apart anterior and posterior surfaces;
said method comprising the steps of:
   (D) creating a cylindrical receptacle in said living cornea corresponding to the shape and size of the optical portion of the prosthetic cornea, which cylindrical receptacle extends from the anterior surface of the living cornea to within the posterior one-third of the stroma thereof;
   (E) creating an annular stromal pocket within the posterior one-third of the stroma, which stromal pocket is continuous with and extends radially outwardly from the receptacle;

(F) placing the prosthetic cornea into the receptacle with said attachment portion situated in said stromal pocket.

30. The method of claim 29 further including the step of making a radial incision into the remaining portion of the living cornea to extend outwardly from the cylindrical receptacle and between the anterior surface of the living cornea and the stromal pocket.

31. The method of claim 30 further including the steps of making a plurality of such radial incisions circumferentially distributed about the cylindrical receptacle to thereby facilitate insertion of the annular flange of the prosthetic cornea into the stromal pocket.

32. The method of claim 30 further including the step of promoting tissue growth from the anterior surface of the living cornea to proceed over the outer surface of the prosthetic cornea by coating at least the outer surface of the prosthetic cornea with a material which stimulates and promotes growth of living tissue.

33. The method of claim 31 further including the step of promoting tissue growth from the anterior surface of the living cornea to proceed over the outer surface of the prosthetic cornea by coating at least the outer surface of the prosthetic cornea with a material which stimulates and promotes growth of living tissue.

34. The method of claim 29 the step of securing includes the substep of allowing the growth of tissue from the living cornea to proceed through the apertures in the annular flange.

35. The method of claim 34 in which the step of securing further includes passing sutures through the living cornea and through the apertures in the annular flange.

36. The method of claim 29 further including the substeps of:

(A) examining the living cornea to determine a correction factor; and
(B) incorporating the correction factor into said prosthetic cornea by providing prosthetic cornea with an optical portion having an inner surface and an outer surface and shaping at least one of the surfaces to provide the correction factor.

37. The method of claim 36 further including the step of making a radial incision into the remaining portion of the living cornea to extend outwardly from the cylindrical receptacle and between the anterior surface of the living cornea and the stromal pocket.

38. The method of claim 37 further including the steps of making a plurality of such radial incisions circumferentially distributed about the cylindrical receptacle to thereby facilitate insertion of the annular flange of the prosthetic cornea into the stromal pocket.

39. The method of claim 37 further including the step of promoting tissue growth from the anterior surface of the living cornea to proceed over the outer surface of the prosthetic cornea by coating at least the outer surface of the prosthetic cornea with a material which stimulates and promotes growth of living tissue.

40. The method of claim 38 further including the step of promoting tissue growth from the anterior surface of the living cornea to proceed over the outer surface of the prosthetic cornea by coating at least the outer surface of the prosthetic cornea with a material which stimulates and promotes growth of living tissue.

41. The method of claim 36 the step of securing includes the substep of allowing the growth of tissue from the living cornea to proceed through the apertures in the annular flange.

42. The method of claim 41 in which the step of securing further includes passing sutures through the living cornea and through the apertures in the annular flange.

* * * * *